United States Patent [19]

Buckler et al.

[11] Patent Number: 4,778,893
[45] Date of Patent: Oct. 18, 1988

[54] OPTICAL INDICATOR 3,4-DIHYDRO-2-QUINOLONES

[75] Inventors: Robert T. Buckler, Edwardsburg, Mich.; Robert P. Hatch, Elkhart, Ind.

[73] Assignee: Miles Inc., Elkhart, Ind.

[21] Appl. No.: 540

[22] Filed: Jan. 5, 1987

Related U.S. Application Data

[63] Continuation of Ser. No. 670,004, Nov. 13, 1984, abandoned, which is a continuation of Ser. No. 475,200, Mar. 14, 1983, abandoned.

[51] Int. Cl.[4] .................. C07D 215/20; C07D 311/02
[52] U.S. Cl. ............................. 546/155; 252/186.41; 422/55; 435/7; 436/66; 436/815; 549/283
[58] Field of Search ........................................ 546/155

[56] References Cited

U.S. PATENT DOCUMENTS 3,547,952 12/1970 Sarkar ........................ 252/301.32
3,891,710 6/1975 Evers et al. ....................... 568/42

OTHER PUBLICATIONS

Sharpless et al., J. Org. Chem. vol. 40, No. 7, 1975, pp. 947–949.
Reich et al., J.A.C.S. 1982, 104, pp. 2936–2937.
J. March, Advanced Org. Chem. 3rd edition, pp. 590, 1107 (1985).
Hori et al., J. Org. Chem. vol 43, No. 9, 1978, pp. 1689–1697.
Toshimitsu et al., Tetrahedron Letters vol. 23, No. 20, pp. 2105–2108 (1982).
Trost et al., JACS, 1976, pp. 4887–4907.
Emerson et al., J. Org. Chem. vol 34, No. 12, 1969, pp. 4115–4118.
Reich et al., J. Org. Chem. vol. 43, No. 9, 1978, pp. 1697–1705.

Primary Examiner—Donald G. Daus
Assistant Examiner—Cecilia Shen
Attorney, Agent, or Firm—Daniel W. Collins; Andrew L. Klawitter

[57] ABSTRACT

Optical indicator chalcogen (selenide or sulfide) compounds responsive to oxidants, e.g., hydrogen peroxide, and methods for preparing and using such indicators. Upon oxidation the resulting intermediate undergoes spontaneous elimination of the chalcogen residue to yield a signal compound which provides an optical signal such as fluorescence. Preferred fluorogenic indicator compounds are 3-chalcogen-3,4-dihydrocoumarin derivatives and 3-chalcogen-3,4-dihydro-2-quinolone derivatives. Such indicator compounds provide highly fluorescent products upon oxidation by hydrogen peroxide and are useful in analytical systems which generate hydrogen peroxide in response to the analyte under determination.

20 Claims, 3 Drawing Sheets

SELENYLCOUMARIN INDICATORS

SELENYLCOUMARIN INDICATORS

SULFENYL-2-QUINOLONE INDICATORS

OPTICAL INDICATOR 3,4-DIHYDRO-2-QUINOLONES

This is a continuation of application Ser. No. 670,004, filed Nov. 13, 1984, now abandoned, which is a continuation of application Ser. No. 475,200, filed Mar. 14, 1983, now abandoned.

BACKGROUND OF THE INVENTION

1. Field of the Invention

The present invention relates to optical indicator compounds, and the methods for their preparation and use, which provide optical signals upon contact with oxidants, particularly hydrogen peroxide. In particular, the invention relates to fluorogenic indicators for hydrogen peroxide and their use in analytical systems, such as diagnostic test systems, which are based on the generation and detection of hydrogen peroxide in response to the analyte under determination.

2. Description of the Prior Art

Many analytical systems involve the measurement of an oxidative substance as the ultimately detected substance. The analyte under determination may itself be such oxidant or the analyte may participate in a chemical, biological, immunological, or the like reaction that produces or destroys a measurable oxidant. These oxidants include substances such as hydrogen peroxide, ozone, periodates, peracids, and superoxides.

In particular, the determination of oxidative enzyme activity is important in analytical chemistry and biochemistry because of its usefulness in clinical diagnostic systems. Among the more commonly studied oxidative enzymes are the oxidases which produce hydrogen peroxide, such as glucose oxidase, xanthine oxidase, and cholesterol oxidase. The hydrogen peroxide generated by the action of such enzymes on their substrates is generally quantitated by oxidation-reduction reactions with various types of optical indicators, usually in the presence of peroxidase. One of the most sensitive means for quantitating hydrogen peroxide is by the use of fluorogenic peroxidase substrates which yield fluorescent products upon peroxidase-catalyzed reaction with hydrogen peroxide.

The literature contains relatively few examples of fluorogenic peroxidase substrates. Some such indicators that have been reported in the literature are homovanillic acid, 3-(p-hydroxyphenyl)propionic acid, 4-amino-1H-1,5-benzodiazepine-3-carbonitrile, and diacetyldichlorofluorescin [K. Zaitsu and Y. Ohkura, *Anal. Biochem.* 109:109(1980), H. Corrodi and B. Weidinius, *Acta Chem. Scand.* 19:1854 (1965), Y. Okamoto et al, *Chem. Pharm. Bull.* 28:2325 (1980), A.S.Keston and R. Brandt, *Anal. Biochem.* 11:1 (1965), and U.S. Pat. No. 4,269,938]. The fluorometric determination of hydrogen peroxide has also been accomplished using the fluorescent compound 6-methoxy-7-hydroxy-1,2-benzopyrone which is oxidized to a nonfluorescent product [W.A. Andreae, *Nature* 175:859 (1955)].

The known fluorogenic peroxidase substrates suffer from several disadvantages, particularly as applied to analytical systems for determining analytes in proteinaceous reaction mixtures, e.g., in immunoassays. Such disadvantages include lack of sensitivity to hydrogen peroxide, instability in aqueous media, excitation wavelengths for the fluorescent product within the range of excitation wavelengths for proteins present in the reaction mixture, and an affinity for binding to proteins present in the reaction mixture.

SUMMARY OF THE INVENTION

The present invention provides a novel class of chalcogen compounds which serve as optical indicators for a variety of oxidants, particularly hydrogen peroxide. The present indicator compounds do not express a particular optical signal, e.g., light absorbance (color) or fluorescence, but upon oxidation by the desired oxidant a different compound is formed which does express the desired optical signal.

The novel compounds of the present invention are, in general, prepared by first obtaining a dihydro-compound which comprises a residue of the formula:

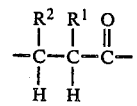

wherein $R^1$ is hydrogen, cyano, carboxyl, alkyl, alkenyl, aryl, carboalkoxy, carboaryloxy, or carboxamide, and $R^2$ is hydrogen, alkyl, alkenyl, or aryl. The dihydro-compound is further characterized by not providing the desired optical signal but, upon an oxidation which replaces the single bond between the carbons bearing the $R^1$ and $R^2$ substituents with a double bond, yields the signal compound. Thus, one can begin by selecting the structure of the desired signal compound, e.g., a highly fluorescent molecule, and by chemical modification thereof or by synthesis from molecules which do not express the signal, prepare a dihydro analog of the signal compound.

Then, in a second step, the dihydro-compound is reacted to sulfenate or selenate the carbon atom bearing the $R^1$ substituent to form the indicator compound wherein the residue depicted above now has the formula:

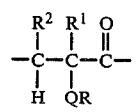

wherein Q is sulfur or selenium (herein referred to as chalcogen) and R is alkyl or aryl, and preferably phenyl or substituted phenyl. Preferably, the depicted residue is part of a cyclic moiety, e.g., a heterocyclic ring, in the indicator compound, which includes coumarins and 2-quinolones. Upon exposure to an oxidant of appropriate oxidation potential, the sulfenyl or selenyl residue attached to the $R^1$ substituent carbon is removed by formation of a sulfoxide or selenoxide intermediate which undergoes spontaneous elimination with generation of a double bond between the $R^1$ and $R^2$ substituent carbon atoms to yield the signal compound.

Where the oxidant is hydrogen peroxide, the present invention provides a particularly advantageous class of coumarin and 2-quinolone chalcogen derivatives which serve as potent fluorogenic indicators of the peroxide. Such compounds have the general formula:

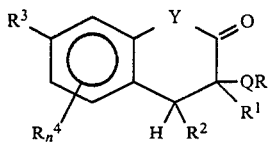 (A)

wherein Q, R, $R^1$ and $R^2$ are as defined above; $R^3$ is $-OR^5$ where $R^5$ is hydrogen or lower alkyl, or $-NR^6R^7$ where $R^6$ and $R^7$, which may be the same or different are hydrogen, alkyl, alkenyl, or aryl; n is an integer from 0 through 3; $R^4$, which may be the same or different when n=2 or 3, is halo, alkyl, alkenyl, alkoxy, or aryl; and Y is $>O$ or $>N-R^8$ wherein $R^8$ is hydrogen or lower alkyl.

The novel chalcogen indicator compounds of the present invention provide particularly potent optical indicators due to the unique application of the sulfoxide and selenoxide elimination reaction. The fluorogenic hydrogen peroxide indicators of formula (A) have particularly advantageous features. The indicator compounds are essentially nonfluorescent, react quickly with hydrogen peroxide in the presence of a peroxidatively active substance such as peroxidase, are nonreactive with peroxidase alone, and are not interfered with by protein binding. The signal compounds produced upon oxidation are highly fluorescent, have excitation and emission wavelengths above that for background protein fluorescence (e.g., above 400 nm), do not form interfering side products, are stable in the presence of hydrogen peroxide and peroxidatively active substances, and do not exhibit interfering protein binding.

DESCRIPTION OF THE PREFERRED EMBODIMENTS

Figure 1:
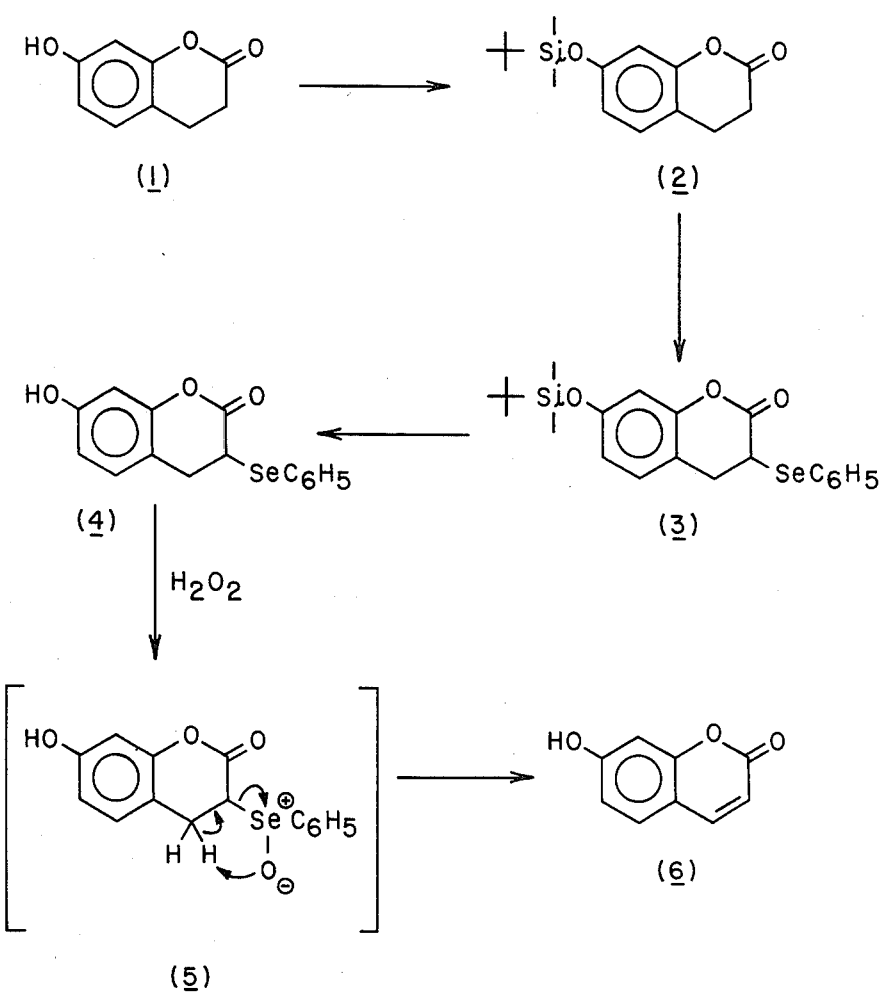
FIGS. 1-3 are flow diagrams of particular synthetic paths for preparing sulfide and selenide indicator compounds of the present invention.

As used herein, "alkyl" is intended to include aliphatic and cyclic organic residues having a carbon atom at the point of attachment which is bonded to one or more hydrogens or one or more carbons or heterocyclic atoms (e.g., nitrogen, oxygen or sulfur) by single bonds. Accordingly, alkyl groups include the unsubstituted hydrocarbon residues of the formula $-C_mH_{2m+1}$ and substituted forms thereof. Such hydrocarbon residues include linear and branched forms and commonly are of the "lower alkyl" aliphatic type wherein m is 6 or less (e.g., methyl, ethyl, n-propyl, iso-propyl, n-butyl, iso-butyl, tert-butyl, n-hexyl, and so forth), but also include higher aliphatic alkyls such as heptyl, octyl, nonyl, and decyl, and the like, as well as cycloalkyls such as cyclopentyl, cyclohexyl, cyclooctyl, and so forth. As stated above, alkyl includes substituted residues which is intended to include the hydrocarbon residues bearing one or more same or different functional groups or substituents as discussed in detail below which are selected so as not to substantially negate the novel features of the present compounds.

"Aryl", as used herein, is intended to include organic residues derived from an aromatic hydrocarbon or heterocyclic ring or ring system by removal of a hydrogen atom. Accordingly, aryl groups include the unsubstituted hydrocarbon ring residues such as phenyl and naphthyl, and substituted forms thereof. Heterocyclic aryl residues are those comprising one or more heteroatoms (e.g., nitrogen, oxygen, or sulfur) in their ring structure, such as pyridyl, triazoyl, furanyl, imidazolyl, quinolinyl, thiophenyl, thiazolyl, oxazolyl, oxadiazolyl, and pyrimidinyl, and substituted forms thereof. It is understood for the purposes of this invention that aryl residues include those bearing one or more same or different functional groups or substituents as discussed in detail below which are selected so as not to substantially negate the novel features of the present compounds.

Further, "alkenyl" includes alkyl groups as defined above wherein at least one C-C single bond is replaced with a C-C double bond, and therefore include the unsubstituted lower alkenyls, e.g., vinyl, 1-propenyl, 2-propenyl, 2-propylidinyl, and so forth, as well as substituted forms thereof. "Alkoxy" and "aryloxy" intend ether linked alkyl and aryl groups, respectively, as defined above (e.g., methoxy, ethoxy, phenoxy). "Carboalkoxy" and "Carboaryloxy" intend carboxyl ester linked alkyl and aryl groups, respectively, as defined above (e.g., acetyl, carbethoxy, benzoyloxy). "Carboxamide" intends unsubstituted and mono- or di-N-substituted amido groups.

In the context of the present invention, used herein, an indication that a particular group (e.g., alkyl, aryl, alkenyl, and the like) is substituted is intended to include such groups when mono- or polysubstituted with functional groups which do not substantially negate the novel features of the present compounds. Such functional groups include essentially all chemical groups which may be introduced synthetically and result in stable indicator compounds. Examples of functional groups are hydroxyl, halo (e.g., fluoro, chloro, bromo), amino (including substituted amino such as alkylamino and dialkylamino), cyano, nitro, thiol, carboxyl [including substituted carboxyl such as substituted and unsubstituted esters (carboalkoxy and carboaryloxy) and carboxamides], alkoxy, aryloxy, alkyl, and aryl.

In general, the present invention is applicable to signal compounds having the residue of the formula:

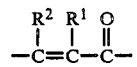

wherein $R^1$ and $R^2$ are as defined above and the carbon-carbon double bond is critical to the chemical or physical properties of the signal compound which yield the detectable optical signal. Such optical signal may be any form of electromagnetic radiation in the infrared, visible, and ultraviolet light regions of the spectrum, for example, light absorption (color), fluorescence, or phosphorescence. One can screen signal compounds for their usefulness in a particular analytical system and then modify the signal compound, or devise a synthetic route, to yield the dihydro-compound which upon sulfenation or selenation gives the indicator compound of the present invention.

The signal compound residue depicted above can form a portion of a linear segment of the signal compound, or, as is more usual, can form a portion of a cyclic moiety of the signal compound. Examples of such cyclic moieties are five, six, and seven-membered carboxyclic and heterocyclic aromatic and nonaromatic rings. Commonly, such cyclic moiety will be a six-membered heterocyclic ring of the formula:

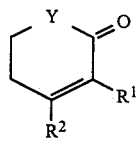

wherein Y is a heteroatom, usually oxygen or nitrogen (when nitrogen such heteroatom will bear hydrogen or a substituent attached to the ring). Such six-membered heterocyclic ring moiety preferably is annealated to an aromatic ring which is usually substituted phenyl.

There are principally two paths for obtaining the necessary dihydro-compound. The first involves direct chemical modification of the signal compound to reduce the carbon-carbon double bond to a single bond, thereby rendering the compound inactive, or substantially so, as a signal generator. The second involves a synthesis of the dihydro-compound from compounds which do not provide the optical signal, and thus which do not include the signal compound.

The sulfenation or selenation step is usually accomplished by treating the dihydro-compound with base and a sulfenyl or selenyl compound of the formula:

X—Q—R wherein Q and R are as defined above and X is halo, e.g., fluoro, chloro, bromo, or iodo; —Q—R; or —NW$_2$ where W is lower alkyl, preferably unsubstituted. See K. B. Sharpless and M. W. Young, *J. Org. Chem.* 40:917 (1975); A. Toshimitsu et al, *Tet. Lett.* 21:5047(1980); D. Liotta et al, *J. Org. Chem.* 46(14):2920(1981); B. M. Trost et al, *J. Am. Chem. Soc.* 98:4887(1976): and H. J. Reich, *Accounts Chem. Res.* 12:22(1979). Particularly preferred sulfenating and selenating agents are substituted or unsubstituted phenylsulfenyl halogens and phenylselenyl halogens such as phenylsulfenyl chloride and phenylselenyl chloride. In the case of a β-dicarbonyl system (i.e., where R$^1$ is carboxyl, carboxyl ester, or amide), the preferred reaction conditions are an equimolar mixture of the phenyl chloride in methylene chloride. A monocarbonyl system is preferably modified by treatment with a strong base such as lithium diisopropylamide at about −78° C., followed by reaction with the phenyl chloride.

The present invention will now be illustrated by particular description of preferred fluorogenic indicators for hydrogen peroxide and their preparation and use. Such indicators have the structure of formula (A) above. Where Y is >O, such compounds are coumarin derivatives, and where Y is >N—R$^8$ are 2-quinolone derivatives.

Fluorogenic indicators (A) where Y is oxygen and R$^3$ is hydroxyl, i.e., umbelliferone derivatives, can be prepared from the appropriate 7-hydroxy-3,4-dihydrocoumarin [V. S. Kamat et al, *Tet. Lett.* 23:154 (1982) and W. D. Langley and R. Adams, *J. Amer. Chem. Soc.* 44:2320(1922)] of the formula:

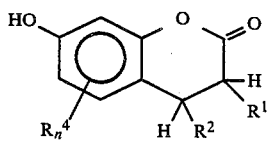

The hydroxyl group is protected in an appropriate manner such as by conversion to its tert-butyldimethylsilyl ether [see compound (2) in FIG. 1] and reacted with the sulfenating or selenating agent X—Q—R. Deprotection of the hydroxyl group yields corresponding indicator compounds (A) which are essentially nonfluorescent. However, upon exposure to hydrogen peroxide and peroxidase, the highly fluorescent coumarins of the formula:

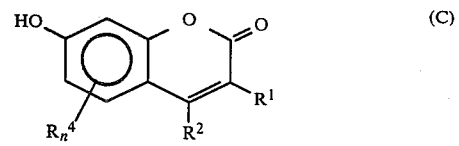

are produced with the concerted loss of the sulfenic or selenenic acid (R—SOH and R—SeOH, respectively) which introduces the critical double bond. Preferably, R is phenyl or substituted phenyl. The R$^1$, R$^2$ and R$^4$ groups can vary widely within the groupings previously described. A wide variety of 3-substituted coumarins [formula (C), R$^1$=CN, COOC$_2$H$_5$, COCH$_3$, C$_6$H$_5$, CONH$_2$, etc.] are known [W. R. Sherman and E. Robins, *Anal. Chem.* 40:803(1968)] or occur naturally in plants ["Heterocyclic Compounds", vol. 2, ed. R. C. Elderfield, John Wiley & Sons (New York 1951) pp. 214–216]. Many such naturally occurring coumarins contain substituents in the benzene ring [formula (C), R$^4$=OH, alkoxy, alkyl, etc.] and others have been made synthetically [J. I. DeGraw et al, *J. Med. Chem.* 11:375(1968); J. Banerji et al, *J. Chem. Soc.* C23:3992(1971); and M.Bandopadkyay et al, *Indian J. Chem.* 12:295(1974)]. Such coumarin derivatives can be converted to the corresponding 3,4-dihydrocoumarin derivatives (B) by catalytic hydrogenation [V. S. Kamat et al, supra] and sulfenated or selenated to give indicator compounds (A) where Y is oxygen and R$^3$ is hydroxyl.

Where Y is oxygen and R$^3$ is —NR$^6$R$^7$, fluorogenic indicators (A) can be prepared by sulfenation or selenation of the appropriate 3,4-dihydrocoumarin with X—Q—R as described above. The required 7-amino-3,4-dihydrocoumarin of the formula:

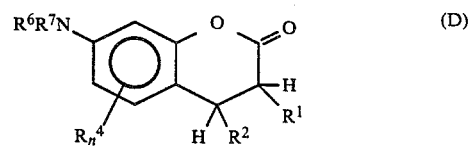

where R$^6$=R$^7$=hydrogen can be obtained by catalytic hydrogenation of the 7-amino or 7-nitrocoumarins. If 7-alkylamino or dialkylamino-3,4-dihydrocoumarins are desired, they can be prepared by N-alkylation of a 7-aminodihydrocoumarin or catalytic hydrogenation of a Schiff base of a 7-aminodihydrocoumarin. Alternatively, the N-alkylaminocoumarin can be prepared using the appropriate 3-alkylaminophenol or 3-dialkylaminophenol as the starting material by the methods described below. The fluorescent species produced upon oxidation by hydrogen peroxide has the formula:

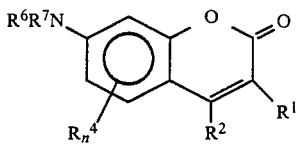

(E)

7-Dialkylaminocoumarins, substituted in the 4-position ($R^2$) with alkyl or aryl, may be synthesized by condensation of a acylacetate with a 3-dialkylaminophenol [A. Darlars, et al, *Ang. Chem. Int. Ed.*, 665(1975). 3-Substituted-7-aminocoumarins can be obtained by Knoevenagel condensation of a 4-amino-2-hydroxy or 2-O-protected benzaldehyde [W. E. Solodar, et al, *J. Org. Chem.* 23:103(1958)]; E. Profft, et al, *Arch. Pharm.* 300:1(1967)]; or the Schiff base [A. A. Goldberg, et al, *J. Chem. Soc.* 2641(1954)]; H. Ichibagase, *J. Pharm. Soc. Jap.* 75:1477(1955); German Pat. No. 1,293,160 (1964) C. W. Schellhammer, K. W. Mueller, R. Rane)]; with acylacetates or malonic esters. In the O-protected case, deprotection is necessary for cyclization to occur.

Fluorogenic indicators (A) where Y is —$NR^8$ and $R^3$ is hydroxyl, i.e., 2-quinolone derivatives, can be prepared from the appropriate 7-hydroxy-3,4-dihydro-2-quinolone [N. Shigematsu, *Chem. Pharm. Bull.* 9:970(1961)] of the formula:

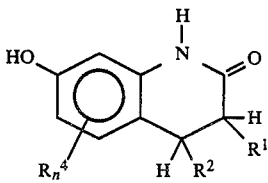

(F)

Figure 2:
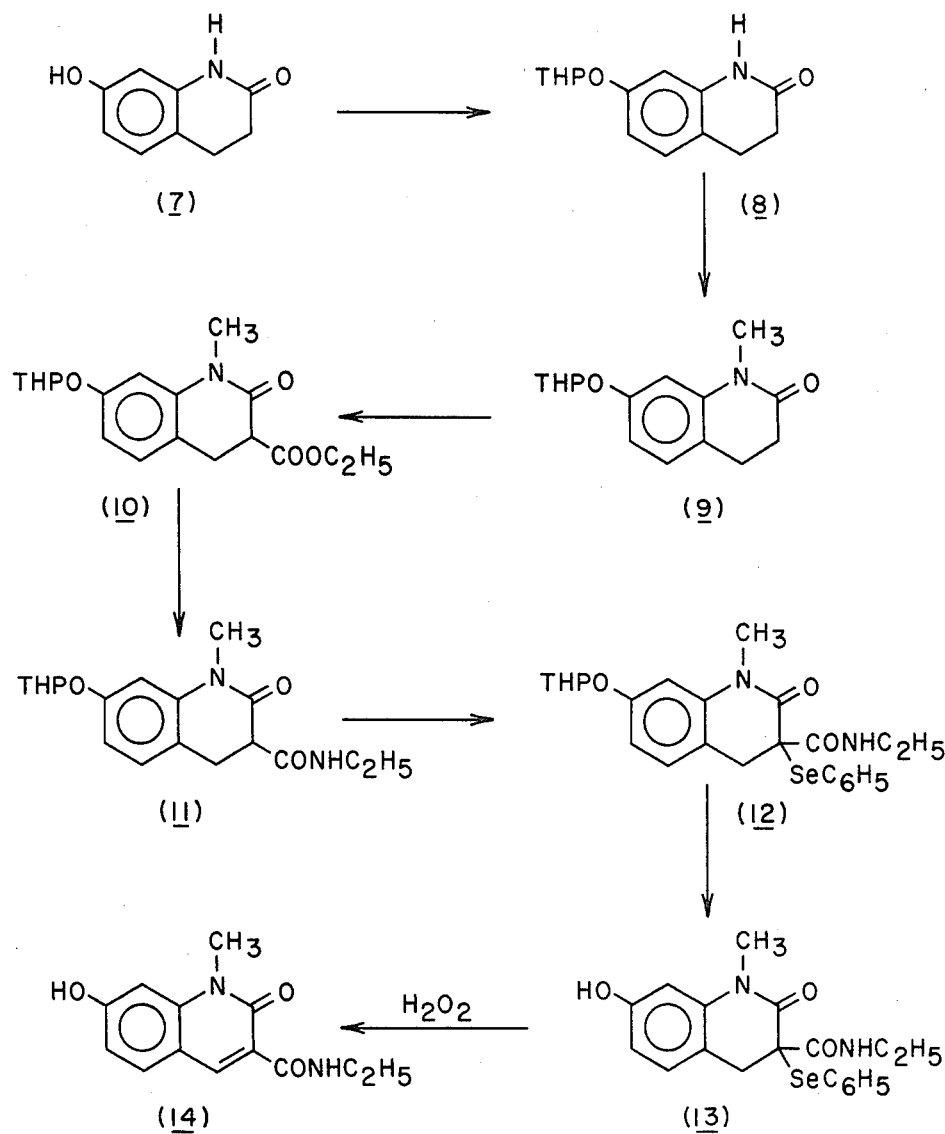

The hydroxyl group is protected in an appropriate manner such as by conversion to its 2-tetrahydropyranyl ether [see compound (8) in FIG. 2]. The protected quinolone can then if desired be N-alkylated such as by treatment with an appropriate substituted or unsubstituted alkyl halide [N. Shigematsu, supra]. Reaction with the sulfenating or selenating agent X—Q—R and deprotection of the hydroxyl group yields corresponding indicator compounds (A) which are essentially nonfluorescent. The fluorescent species produced upon oxidation by hydrogen peroxide has the formula:

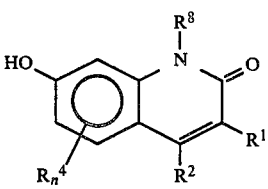

(G)

The $R^1$, $R^2$ and $R^4$ groups can vary widely within the groupings previously described. 3-Substituted dihydroquinolones [formula (G), $R^1$=carboxyl, or substituted or unsubstituted carboxamide and alkyl carboxyester] can be prepared by known transformations of the carbethoxy group whose method of introduction is disclosed in the Examples which follow. Also, the 7-hydroxyl group can be replaced with 7-(lower alkyl) amino substituents with various derivatives being known [N. Shigematsu, supra; H. Veda and Z. H. Yan, *J. Taiwan Pharmaceut. Assoc.* 1:88(1949), Y. Tamura et al, *Chem. Ind.* (London) 1975, 922; and G. S. Sidhu et al, *Annalen* 627:224(1959).

With reference to formula (A) depicting the structure of preferred fluorogenic indicators of the present invention, the various R, $R^1$, $R^2$, etc. Substituent groups can vary widely without departing from the inventive features of the present invention.

The substituent R generally will be selected from substituted or unsubstituted alkyl, usually methyl, or aryl (e.g., phenyl and pyridyl). Substituted phenyls include phenyl substituted with one or more electron withdrawing groups such as halo or nitro or other groups which improve the elimination of the sulfenyl or selenyl residue upon oxidation of the indicator compounds.

The $R^1$ substituent can vary quite widely and generally will be hydrogen, cyano, carboxyl, alkyl, normally lower alkyl, alkenyl, also normally lower alkenyl, aryl, carboalkoxy, carboaryloxy, or carboxamide. The carboxyl esters are principally alkyl esters such as carbomethoxy, carbethoxy, and so forth, and carboxamide includes substituted amides such as N-alkylcarboxamides and N-aralkylcarboxamides—e.g., N-ethylcarboxamide, N-butylcarboxamide, N-benzylcarboxamide, N-phenethylcarboxamide, and N-2-pyridylmethyl-carboxamide. Preferably, $R^1$ is of the formula —$CONHR^9$ wherein $R^9$ is hydrogen or substituted or unsubstituted alkyl or aryl.

Likewise, a wide variety of functional groups can comprise the $R^2$ substituent. Usually $R^2$ will be hydrogen, alkyl, normally unsubstituted lower alkyl or fluorosubstituted lower alkyl (e.g., trifluoromethyl), alkenyl, again normally lower alkenyl, or aryl.

The $R^4$ substituents can be selected from those known to exist in coumarins and 2-quinolones found in nature or capable of being synthesized to give fluorogenic indicators. The $R^4$ substituents, if present, (i.e., where n is greater than or equal to 1), occupy the 5-, 6-, and 8-position on the ring nucleus. When an $R^4$ substituent is not present at any one or more of such positions, they are occupied by hydrogen. When n=1, the $R^4$ substituent can be at any of the 5-, 6-, and 8-positions, commonly at the 5- or 6-position, and preferably at the 6-position. When n=2, the two $R^4$ substituents can be at the 5- and 6-, the 5- and 8-, or the 6- and 8-positions, and can be the same or different. Such $R^4$ substituents include halo (fluoro, chloro, bromo) alkyl, normally unsubstituted lower alkyl, alkenyl, again normally unsubstituted lower alkenyl, alkoxy (preferably unsubstituted lower alkoxy such as methoxy and ethoxy), or aryl. In general, the $R^4$ substituents can include any organic radical or functional group which either enhances or does not significantly negate the fluorescent properties desired in the signal compound produced upon elimination of the sulfenyl or selenyl residue.

A preferred subset of fluorogenic indicators of hydrogen peroxide are those of the formula:

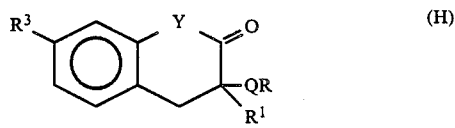

(H)

wherein Q is sulfur or selenium, R is alkyl, phenyl, or substituted phenyl; $R^1$ is hydrogen, cyano, or is of the formula —$COOR^9$, —$CONHR^9$, or —$CON(R^9)_2$ where R⁹ is hydrogen, alkyl, alkenyl, or aryl; R³ is —OH or —NR⁶R⁷ where R⁶ and R⁷, which can be the same or different, are hydrogen or lower alkyl, and Y is >O or >N—R⁸ where R⁸ is hydrogen or lower alkyl.

Particularly preferred indicator compounds are those of formula (A) wherein Q=sulfur or selenium, n=0, and R²=hydrogen, and the remaining substituents are selected from any combination of the following:

| R | R¹ | Y | R³ |
|---|---|---|---|
| (phenyl) | —COOalkyl<br>—COOH | O (=O) | —OH |
| (O₂N-phenyl) | —CONH₂<br>—CONHalkyl | H-N< | —OCOalkyl |
| (N-pyridyl) | —CON(alkyl)₂<br>—CN | alkyl-N< | —NH₂<br>—NHalkyl<br>—N(alkyl)₂ |

The novel chalcogen compounds of the present invention are useful as optical indicators for oxidants. Accordingly, the compounds find use in analytical systems for detecting or determining, qualitatively or quantitatively, either an oxidant capable of oxidizing the present compounds with elimination of the sulfenyl or selenyl residue or an analyte which participates in a reaction, e.g., a chemical, biological, or immunological reaction, to produce or destroy such an oxidant. Such oxidant is exemplified by substances such as ozone, periodates, peracids, superoxides, hydroperoxides, organic peroxides, and, in particular, hydrogen peroxide.

The present invention provides particularly advantageous hydrogen peroxide-sensitive indicators for use in analytical systems in the diagnostic field. Numerous diagnostic test systems are known which are based ultimately on the determination of hydrogen peroxide. For example, there are the determinations of various analytes such as glucose, galactose, cholesterol and uric acid, based on the action of specific oxidase enzymes (e.g., glucose oxidase, galactose oxidase, cholesterol oxidase, uricase). Similarly, there are enzymatic test systems in which the analyte is reacted enzymatically or nonenzymatically to produce a product which in turn is reacted in one or more enzymatic or nonenzymatic steps to yield ultimately hydrogen peroxide. By appropriate selection of an indicator compound the resulting optical signal may be a color change, or, most advantageously, fluorescence as a function of hydrogen peroxide concentration.

Furthermore, the present indicators are applicable to specific binding assays such as immunoassays in which a labeling substance is used which is detectable by generation of hydrogen peroxide. Such binding assay systems include those in which the label is an oxidase enzyme or an enzyme which produces a product which is then acted on enzymatically or nonenzymatically to yield hydrogen peroxide. Examples of such systems are the heterogeneous and homogeneous enzyme-labeled immunoassays described in the literature such as in U.S. Pat. Nos. 3,654,090 and 3,817,837. Alternatively, the label can be a substrate, an inhibitor, a coenzyme, or a prosthetic group for such an enzyme, as described in U.S. Pat. Nos. 4,279,992; 4,238,565; 4,134,792 and 4,273,866 and in U.K. Pat. Spec. No. 1,552,607.

It is preferred that the test sample or reaction mixture containing hydrogen peroxide to be determined with the present indicator compounds also be contacted with a peroxidatively active substance as is known in the field. Plant peroxidases, such as horseradish peroxidase or potato peroxidase, can be used. Inorganic compounds having peroxidase activity include iodides, such as sodium and ammonium iodides, and molybdates. In addition, urohemin and a number of other porphyrin substances having peroxidase activity can be used.

The present invention will now be illustrated, but is not intended to be limited, by the following examples.

EXAMPLES

Preparation of Optical Indicator Selenide and Sulfide Compounds

Figure 3:
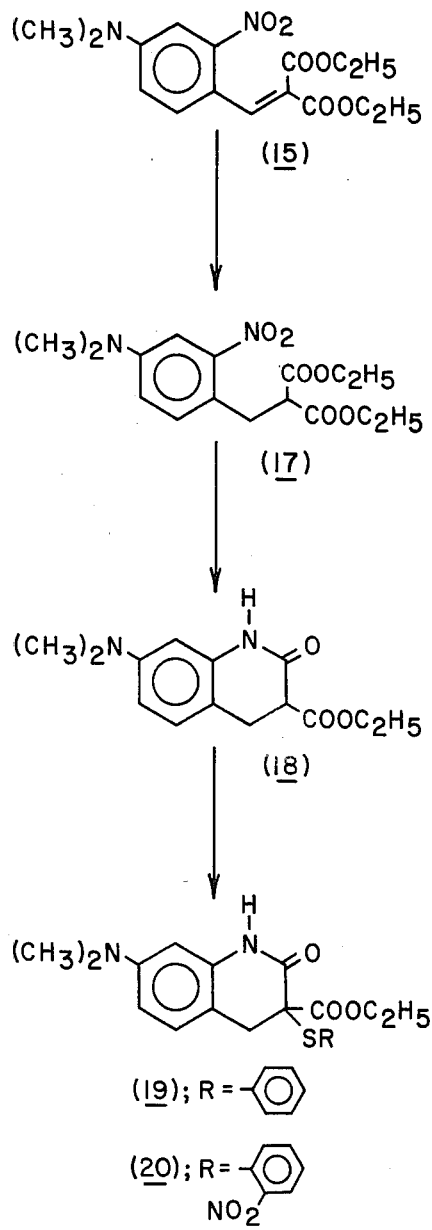

Italized numbers in parentheses refer to the structural formulae in the diagrams of FIGS. 1-3 and/or are used in the Table at the conclusion of the Examples.

7-HYDROXY-3-PHENYLSELENYL-3,4-DIHYDROCOUMARIN (4)

A solution of 5 grams (g) [30 millimoles (mMol)] of 7-hydroxy-3,4-dihydrocoumarin (1) [W. D. Langley and R. Adams, *J. Amer. Chem. Soc.* 44:2320 (1922)] 5.2 g (76.4 mMol) of imidazole, and 5.45 g (36 mMol) of tert-butyldimethylsilyl chloride in 30 milliliters (mL) of dry dimethylformamide (DMF) was stirred at room temperature for 16 hours. The solvent was then removed under reduced pressure. The residue was dissolved in methylene chloride and washed with 3 normal (N) hydrochloric acid (HCl) followed by saturated aqueous sodium bicarbonate (NaHCO₃) solution. The organic solution was dried over anhydrous magnesium sulfate (MgSO₄), filtered, and evaporated to leave a residue which was distilled to give 5.5 g (61% yield) of the silyl ether (2) as a clear oil, b.p. 90°-105° C./1 torr. It crystallized on standing to produce a white solid, m.p. 46°-47° C.

Lithium diisopropylamide (LDA) was generated by the dropwise addition of 9.5 mL (14.7 mMol) of a 1.55 molar (M) solution of n-butyl lithium in hexane to a −20° C. solution of 1.49 g (2.1 mL, 14.8 mMol) of diisopropylamine in 35 mL of dry tetrahydrofuran (THF). The solution was cooled to −78° C. while stirring under an inert atmosphere, and to it was added dropwise 3.74 g (13.4 mMol) of the silyl ether (2) in 35 mL of THF. After 15 minutes, a solution of 3.3 g (17.4 mMol) of phenylselenyl chloride (PhSeCl) (Aldrich Chemical Co., Milwaukee, WI) in 25 mL of THF was added dropwise. The dark red color of the phenylselenyl chloride disappeared immediately upon addition. After 20 minutes, the reaction was allowed to warm to room temperature and stirred for 90 minutes. Two mL of concentrated HCl in 10 mL of H₂O was added followed by 300 mL of chloroform (CHCl₃). The solution was washed with 3 N HCl, saturated NaHCO₃ solution, dried over anhydrous MgSO₄, filtered, and evaporated. The residue was chromatographed on 300 g of silica gel eluting with 1:1 (v/v) CHCl₃:hexane. Eighteen mL fractions were collected. Fractions 91-160 were pooled and evaporated to yield 1.68 g of the selenium derivative (3). It was not characterized but was dissolved in 25 mL of dry THF and combined with 3.6 mL of a 1 M THF solution of tetra-n-butylammonium fluoride. After 30 minutes at room temperature, 0.4 mL of glacial acetic acid was added, and the reaction diluted with 75 mL of $CHCl_3$. The solution was washed with saturated $NaHCO_3$, dried, and evaporated. The oily residue was chromatographed on 200 g of silica gel eluting with 19:1 (v/v) methylene chloride ($CH_2Cl_2$):ether. Eighteen mL fractions were collected. Fractions 75-95 were combined and evaporated to give 300 milligrams (mg) of selenide (4) as a white solid, m.p. 154°-157° C.

7-Hydroxy-3-(N-ethylcarboxamido)-3-phenylselenyl-N-methyl-3,4-dihydro-2-quinolone (13)

To a slurry of 1 g of 7-hydroxy-3,4-dihydro-2-quinolone (7) [N. Shigematsu, *Chem. Pharm. Bull.* 9:970 (1961)] in 8 ml of dry dioxane was added 8 mL of dihydropyran and 5 mg of p-toluenesulfonic acid. The reaction was stirred under an inert atmosphere for 90 minutes, then diluted with 150 mL of $H_2O$. It was extracted with three 50 mL portions of ether, and the combined extracts dried over anhydrous $K_2CO_3$. Filtration and evaporation gave 2 g of an oil which crystallized when triturated with hexane. When dry it amounted to 1.18 g (78% yield) of white crystals of the 2-tetrahydropyranyl ether (8), m.p. 129°-131° C.

A slurry of 2.47 g (10 mMol) of (8) and 228 mg of benzyltriethylammonium chloride in a mixture of 50 mL of toluene and 4 mL of a solution of 1 g of NaOH in 1 mL of $H_2O$ was stirred under an inert atmosphere at room temperature. Methyl iodide (1.26 mL 20 mMol) was added and the reaction stirred rapidly for 20 hours at 47° C. (oil bath). It was then diluted with 250 mL of cold $H_2O$. The aqueous phase was separated and washed with two 75 mL portions of $CHCl_3$. The $CHCl_3$ extracts were combined with the toluene phase, dried, and evaporated. The oily residue was crystallized from hexane to give 2.56 g (93% yield) of (9) as a white solid, m.p. 53°-55° C.

A solution of 0.315 mL of freshly distilled isopropylcyclohexylamine in 2 mL of dry THF was placed in a 25 mL flask. A second solution was prepared by dissolving 0.315 mL of the same amine in 1.5 mL of THF in a 5 mL flask. Both solutions were cooled to −78° C. while stirring under an inert atmosphere and treated with 1.2 mL of a 1.6 M hexane solution of n-butyl lithium, dropwise from a syringe over 1.5 minutes in order to form lithium isopropylcyclohexylamide. To the first solution was added, dropwise over 6 minutes, 500 mg of (9) in 1 mL of THF. The reaction was stirred at −78° C. for 5 minutes, then a solution of 0.12 mL of diethyl carbonate in 0.5 mL of THF was added, dropwise over 10 minutes via syringe. After 3 additional minutes, the second solution of lithium isopropylcyclohexylamide was added followed by an additional 0.12 mL of diethyl carbonate. After 20 minutes at −78° C., the reaction was allowed to warm to room temperature and stir for 10 minutes following which it was neutralized with 0.2 mL of acetic acid in 2 mL of $H_2O$. The reaction was partitioned between 100 mL of $H_2O$ and 35 mL of ether. The ether phase was separated, dried, filtered, evaporated, and the residue dried under high vacuum to give a yellow oil. It was chromatographed on 60 g of silica gel eluting with 29:1 (v/v) $CH_2Cl_2$:EtOH. Nine mL fractions were collected. Fractions 29-51 were combined and evaporated to give 548 mg (86% yield) of the ester (10) as a clear, pale-yellow oil.

To a solution of 360 mg of the ester (10) in 5.3 mL of methanol was added 5.31 mL of 70% aqueous ethylamine. After 25 hours at room temperature, solvent was evaporated to give an oil. It was chromatographed on 62 g of silica gel eluting with 19:1 (v/v) $CH_2Cl_2$: EtOH, collecting 7 mL fractions. Fractions 34-42 were combined and evaporated to give 289 mg (74% yield) of the N-ethylamide (11) as an oil.

A solution was prepared by dissolving 102 mg of phenylselenyl chloride in 2 mL of dry $CH_2Cl_2$. It was cooled to −20° C. and combined with 0.044 mL of pyridine in 1 mL of $CH_2Cl_2$. To this was added, dropwise via syringe over 4 minutes a solution of 175 mg of (11) in 2 mL of $CH_2Cl_2$. The reaction was allowed to warm to room temperature and stir for 18 hours. It was concentrated under reduced pressure to leave an oil which was chromatographed on 22 g of silica gel. The column was eluted with 10:1 (v/v) $CH_2Cl_2$:ethyl acetate, and 7 mL fractions were collected. Fractions 39-55 were pooled and evaporated to give 94 mg (39% yield) of 3-(N-ethylcarboxamido)-3-phenylselenyl-7-(2-tetrahydropyranyloxy)-N-methyl-3, 4-dihydro-2-quinolone (12) as an oil.

A solution of 92 mg of (12) in 0.67 mL of THF was combined with 0.67 mL of acetic acid and 0.67 mL of $H_2O$. After stirring for 6 hours under an inert atmosphere, the solvent was removed on a rotary evaporator. Five mL of $H_2O$ was added and removed under reduced pressure, and the process was repeated. The residual oil was crystallized from ether to give 53 mg (70% yield) of 7-hydroxy-2-(N-ethylcarboxamido)-3-phenylselenyl-N-methyl-3, 4-dihydro-2-quinolone (13) as white solid, m.p. 140°-141° C.

Ethyl-α-carbethoxy-4-dimethylamino-2-nitrocinnamate (15)

A mixture of 89 g (0.5 mol) of 4-dimethylamino-2-nitrobenzaldehyde [H. Baumann, et al German Pat. 2,363,458], 237 g (1.4 mol) of diethyl malonate, 3.44 g (40.4 mmol) of piperidine and 2.43 g (40.4 mmol) of acetic acid in 400 mL of toluene was refluxed for 16 hours under argon, with a Dean Stark trap attached. The solution was cooled to room temperature and washed with 200 mL of 5% aqueous KOH. The organic phase was separated, dried over sodium sulfate ($Na_2SO_4$), filtered, and the solvent evaporated. The dark red solid residue was dissolved in 40 mL of $CH_2Cl_2$ and 100 mL of hexane added. After standing for 1 hour, the solution was filtered to yield 10.4 g of orange crystals. Recrystallization from $CH_2Cl_2$ - hexane produced an analytical sample, m.p. 101°-102° C.

Analysis: Calculated for: $C_{16}H_{20}N_2O_6$; C, 57.14; N, 5.99; N, 8.33. Found: C, 57.65; H, 6.12; N, 8.34.

$^1$H NMR ($CDCl_3$)δ: 8.08 (s, 1H); 7.3–7.5 (m, 2H); 6.84 (dd, J=3, 8Hz, 1H); 4.34 (q, J=8, 2H); 4.23 (q, J=8, 2H); 3.10 (s, 6H); 1.27 (q, J=8, 6H).

7-Dimethylamino-3 (N-ethylcarboxamido)-2-quinolone

A mixture of 1.0 g (3.0 mmol) of the preceeding cinnamate ester (15), 40 mL of absolute EtOH, 1 mL of $H_2O$, 0.4 mL of conc HCl, and 1.5 g (26.9 mg-atm) of iron filings was refluxed under argon for 2.5 hours. An additional 1.7 g (30.4 mg/atm) of iron filings was added and the heating continued for 3 hours. The mixture was filtered while hot and the filtrate evaporated. The residue was dissolved in 50 mL of 2.55 M methanolic HCl and allowed to stand for 20 minutes at room temperature. Solvent was then evaporated and the residue partitioned between 150 mL CHCl₃ and 50 mL saturated NaHCO₃ solution. The organic phase was separated and the aqueous phase washed with 75 mL of CHCl₃. The organic phases were combined, dried (Na₂SO₄), filtered and evaporated to yield 0.49 g of a dark brown solid. The aqueous phase was extracted with 120 mL of isobutanol, which when dried (Na₂SO₄) filtered and evaporated, yielded an additional 0.08 g. The two residues were slurried in 30 mL of MeOH and 10 mL of 70% ethyl amine (EtNH₂)-30% H₂O were added. The mixture was stirred for 3 days at room temperature, then was placed in a stainless steel bomb and heated at 100° C. for 6 hours. After evaporation of the solvent, the residue was chromatographed on 75 g of silica gel, eluting with 19:1 (v/v) $CH_2Cl_2$:MeOH. Fractions 25–34 (7 mL/fraction) were combined and concentrated to a volume of 7 mL. Filtration yielded 0.19 g of yellow needles, m.p. 299°–300° C.

Analysis: Calculated: $C_{14}H_{17}O_2N_3$: C, 74.85; H, 6.61; N, 16.20 Found : C, 74.84; H, 6.74; N, 16.19.

hu 1H NMR (CDCl₃)δ: 7.53 (d, J=9Hz, 1H); 6.60 (dd, J=4, 9Hz, 1H); 6.40 (broad x, 1H); 3.53 (m, 2H); 3.10 (s, 6H); 1.26 (t, J=7, 3H).

7-Dimethylamino-3-(N-ethylcarboxamido)-1-methyl-2-quinolone

To a suspension of 10 mg (0.2 mmol) of hexane washed 50% sodium hydride (NaH) oil dispersion in 1 mL of dry dioxane, was added a slurry of 50 mg (0.2 mmol) of the preceeding quinolone in 2 mL of a 1:1 mixture of dioxane-DMF. The mixture was allowed to stir for 30 minutes at room temperature, then 0.57 g (4 mmol) of iodomethane was added rapidly. After allowing the reaction to stir for 30 minutes, the solvent was evaporated and the residue dissolved in 50 mL of CHCl₃. The solution was washed with 30 mL of H₂O and the organic layer was dried (Na₂SO₄) filtered and evaporated. Precipitation of the product occurred when the residue was dissolved in 5 mL of CHCl₃ and triturated with 20 mL of diethyl ether. Filtration yielded 32 mg of a yellow solid, m.p. 248°–251° C. Recrystallization from ethanol yielded yellow needles m.p. 252°–253° C.

Analysis: Calculated: $C_{15}H_{21}N_3O_2$: C, 75.91; H, 7.00; N, 15.37. Found: C, 75.08, H, 6.93; N, 15.31.

¹H NMR (CDCl₃)δ: 8.40 (s, 1H); 7.58 (d, J=9, 1H); 6.68 (dd, J=4, 9, 1H), 6.23 (broad d, J=4, 1H); 3.67 (s, 3H); 3.2–3.7 (m, 2H); 3.13 (s, 6H); 1.26 (t, J=8, 3H).

7-Dimethylamino-3-(N-ethylcarboxamido)-3,4-dihydro-3-phenylselenyl-1-methyl-2-quinolone (16)

A mixture of 0.3 g (1.15 mmol) of the preceeding 2-quinolone and 0.1 g (2.6 mmol) of sodium borohydride (NaBH₄) in 25 mL of absolute EtOH was allowed to stir for 24 hours. Two additional 0.1 g portions of NaBH₄ were added and stirring continued for 24 hours; then a fourth 0.1 g portion of NaBH₄ was added and the reaction warmed to 70° C., and allowed to stir for 17 hours. At this time 0.3 g of NaBH₄ was added to the reaction in 0.1 g portions at 4 hour intervals, and the reaction was allowed to stir overnight at 70° C. The solvent was evaporated and the residue chromatographed on 100 g of silica gel, eluting with 2.5% CH₂OH-97.5% CH₂Cl₂. Fractions 55–85 (12 ml/fraction) were combined and evaporated to yield a yellow oil. Diethyl ether was added and evaporated to yield a yellow solid, m.p. 105°–107° C.

Analysis: ¹H NMR (CDCl₃)δ: 7.10 (d, J=8, 1H); 6.43 (dd, J=4,8, 1H); 6.33 (s, 1H); 3.40 (s, 3H); 3.24 (m, 5H); 2.97 (s, 6H); 1.18 (t, J=8, 3H).

A solution of 0.1 g (0.36 mmol) of the dihydroquinolone was dissolved in 3 mL of CH₂Cl₂ and added to a cooled (−20°) solution of a PhSeCl-pyridine complex in 3 mL of CH₂Cl₂, which had been formed by dropwise addition of 0.034 g (0.44 mmol) of pyridine to a cooled (−20°) solution of 0.083 g (0.44 mmol) PhSeCl in 3 mL of CH₂Cl₂. The reaction was allowed to warm to room temperature and stir for 1 hours. It was then placed directly on a 40 g silica gel column and eluted with 2% MeOH - 98% CH₂Cl₂. Fractions 24–33 (10 mL/fraction) were combined and evaporated to yield 90 mg of a white solid. This was rechromatographed on 75 g of silica gel, eluting with 1% MeOH - 99% CH₂Cl₂. Fractions 51–71 (10 mL/fraction) were combined and evaporated to yield a glass. Trituration with diethyl ether produced 21 mg of a white solid, m.p. 126°–127° C.

Analysis: ¹H NMR (CDCl₃)δ: 7.67–7.25 (m, 7H); 6.7 (s, 1H); 3.36 (s, 3H); 3.4–2.93 (m, 4H); 2.77 (s, 6H); 1.13 (t, J=8, 3H).

7-Dimethyl-3-carbethoxy-3,4-dihydro-2-quinolone (18)

To a slurry of 5.0 g (14.8 mmol) of the cinnamate ester (15) in 100 mL of absolute ethanol was added 0.34 g (9.2 mmol) of NaBH₄. The mixture was allowed to stir for 2.5 hours at room temperature then 1 mL of glacial acetic acid (AcOH) added and the solvent removed under reduced pressure. The residue was dissolved in 250 mL of CHCl₃ and washed with 100 mL of saturated NaHCO₃ solution. After washing with 100 mL of H₂O, the organic phase was dried (Na₂SO₄), filtered and the solvent evaporated under reduced pressure to yield 4.86 g of the crude dihydrocinnamate (17) as a dark red oil. Dioxane (50 ml) was added and the solution concentrated. The oily residue was dissolved in 50 ml of dioxane and 0.5 g of 10% Pd on C added. The mixture was shaken under 50 p.s.i. of H₂ at 50° C. for 6.5 hours. After the reaction had cooled to room temperature, the catalyst was removed by filtration through Celite and the solvent was concentrated to a volume of 25 mL. Diethyl ether (5 mL) was added and the solution allowed to stand overnight. Filtration produced 2.3 g of the product (18) as a white solid, m.p. 181°–182° C.

7-Dimethylamino-3-carbethoxy-3-phenylsulfenyl-3,4-dihydro-2-quinolone (19)

To a cooled (−78° C.) solution of 0.022 g (0.22 mmol) of diisopropylamine in 2 mL of THF was added 0.12 mL of 1.6 M n-butyllithium in hexane (0.19 mmol). After 15 minutes, 0.05 g (0.19 mmol) of the ester (18) in 2 mL of THF was added. The reaction was stirred for 0.5 hours at −78° C. under nitrogen (N₂). Phenylsulfenyl chloride (0.1 ml) (prepared by the method described in *Reagents for Organic Synthesis*, ed. Fieser & Fieser, Vol. 5, John Wiley & Sons (1975) p. 523) was added dropwise and the reaction mixture stirred for 20 minutes, then allowed to warn to room temperature. Water (5 mL) was then added and the mixture extracted twice with 5 mL of ethyl acetate (EtOAc). The combined extracts were dried (Na₂SO₄), filtered and the solvent removed under reduced pressure. The residue was purified by preparative thin layer chromatography (prep. T.L.C.), eluting with 9/1 CHCl₃/EtOAc. The band corresponding to $R_F$=0.14 was collected and washed with CH$_3$OH to yield 0.016 g of the sulfide (19) as a yellow powder, m.p. 134°–139° C.

7-Dimethylamino-3-carbethoxy-3-(0-nitrophenylsulfenyl)-3,4-dihydro-2-quinolone (20)

To a cooled (−78° C.) solution of 0.022 g (0.22 mmol) of diisopropylamine was added 0.12 mL of 1.6 M n-butyllithium in hexane (0.19 mmol). After 15 minutes, 0.05 g (0.19 mmol) of the ester (18) in 2 ml of THF was added. The reaction was stirred for 0.5 hours at −78° C. under N$_2$, then 0.037 g (0.16 mmol) of 0-nitrobenzenesulfenyl chloride (Aldrich Chemical Co.) in 2 mL of THF was added. After the reaction had stirred for 20 minutes at −78° C., it was allowed to warm to room temperature. Water (5 mL) was added and the mixture extracted twice with 5 mL of EtOAc. The extracts were combined, dried (Na$_2$SO$_4$), and the solvent removed under reduced pressure. The residue was purified by prep. T.L.C., eluting with 20/1-CHCl$_3$/EtOAc. The band corresponding to R$_F$=0.1 was scraped from the plate and the product was washed off with CH$_3$OH (100 mL). The product (20) crystallized when the solution was allowed to stand overnight to yield 0.03 g of yellow-orange crystals, m.p. 174.5°–175.5° C.

7-Acetoxy-3-carbethoxy-3-phenylselenyl-3,4-dihydrocoumarin (21)

To a slurry of 5.0 g (21 mMol) of 3-carbethoxy-7-hydroxycoumarin [H. Pechmann and E. Graezer, *Chem. Ber.* 34:378 (1901)9 in 100 mL of CH$_2$Cl$_2$ containing 5 mL of ethylvinyl ether was added 30 mg of p-toluenesulfonic acid. After 15 minutes, the reaction was poured into 100 mL of 10% potassium hydroxide (KOH) solution. The organic phase was separated, washed with H$_2$O, dried and evaporated. The residue was taken up in toluene and precipitated with hexane to give 1.73 g (26% yield) of the 1-ethoxyethyl ether as a solid, m.p. 70°–71° C.

A solution of 12.6 g (12.6 mMol) of lithium tri-(sec-butyl)borohydride in 20 mL of THF was cooled in a dry ice-acetone bath while stirring under an inert atmosphere. To this was added a solution of 3.2 g (10.5 mMol) of the 1-ethoxyethyl ether in 45 mL of THF. After 30 minutes at this temperature, 0.75 mL (12.5 mMol) of glacial acetic acid was added and the solution allowed to warm to room temperature. It was diluted with 200 mL of CHCl$_3$ and washed with aqueous NaHCO$_3$ solution. The organic phase was dried, filtered, and evaporated to give a residue which was chromatographed on 250 g of silica gel eluting first with 500 mL of CH$_2$Cl$_2$, then with 3 L of 19:1 (v/v) CH$_2$Cl$_2$:THF. Twenty mL fractions were collected. Fractions 91–115 were pooled and evaporated to yield 1.1 g (45%) of 7-hydroxy-3-carbethoxy-3,4-dihydrocoumarin (21), m.p. 106°–108° C.

A solution of 1 g (4.2 mMol) of this phenol in 10 mL of pyridine was combined with 2 mL of acetic anhydride and allowed to stand for 30 minutes at room temperature. Evaporation gave a white solid of the acetate ester, m.p. 125°–127° C., which was used without further purification. 600 mg of it was dissolved in 10 mL of CH$_2$Cl$_2$ and added to a −20° C. slurry of 430 mg (2.2 mMol) of phenylselenyl chloride and 170 microliters (μL) of pyridine. After 15 minutes at this temperature, the reaction was allowed to warm to room temperature and stir for 2 hours. It was then applied directly to a column of 100 g of silica gel, and eluted with 19:1 (v/v) CH$_2$Cl$_2$:acetone. The product eluted within the first 500 mL. Crystallization from ether-hexane gave 7-acetoxy-3-carbethoxy-3-phenylselenyl-3,4-dihydrocoumarin as a crystalline solid, m.p. 110°–112° C.

7-Acetoxy-3-(N-ethylcarboxamido)-3-phenylselenyl-3,4-dihydrocoumarin (22)

3-Carbethoxy-7-hydroxycoumarin (10 g, 43 mMol) was suspended in 60 mL of dry methanol while stirring under an inert atmosphere at 0° C. To this was added dropwise 15 mL of anhydrous ethylamine. After 1 hour, a homogenous solution resulted. An additional 15 mL of ethylamine was added and the solution stirred at room temperature for 2 hours. Evaporation of the solvent left a residue which was taken up in 400 mL of H$_2$O and combined with 60 mL of 1 N acetic acid. A white precipitate formed, and the mixture (pH 4.3) was stored at 4° C. for 18 hours. The precipitate was collected by filtration, washed with H$_2$O, and dried in vacuum at 56° C. to give 8.57 g (86% yield) of 3-(N-ethylcarboxamido)-7-hydroxycoumarin as a cream colored solid, m.p. 258°–260° C. Five grams of this substance was suspended in 100 mL of CH$_2$Cl$_2$ containing 15 mL of dihydropyran and 90 mg of p-toluenesulfonic acid. After stirring for 2 hours at room temperature, 1 mL of triethylamine was added, and the solvent evaporated under reduced pressure. The residue was dissolved in 150 mL of CHCl$_3$, and the solution washed with 10% KOH solution, dried and evaporated. The product crystallized to yield 3.8 g (50%) of the 2-tetrahydropyranyl (THP) ether of 3-(N-ethylcarboxamido)-7-hydroxycoumarin, m.p. 164°–167° C.

A solution of lithium tri-(sec-butyl)borohydride (28.7 mL 28.7 mMol) in THF was diluted with 20 mL of THF, and cooled in an acetone-dry ice bath while stirring under an inert atmosphere. To it was added 7.6 g (24 mMol) of the THP ether dissolved in 200 mL of THF. After 30 minutes at this temperature, 1.7 mL (28 mMol) of glacial acetic acid was added and the reaction allowed to warm to room temperature. It was then partitioned between 250 mL of saturated aqueous NaHCO$_3$ solution and 400 mL of CHCl$_3$. The organic phase was separated, dried, filtered, and concentrated to a volume of 30 mL. This was applied directly to a 300 g silica gel column and eluted with 200 mL of 19:1 (v/v) CH$_2$Cl$_2$:THF followed by 9:1 CH$_2$Cl$_2$:THF. Twenty mL fractions were collected. Fractions 100–145 were pooled and evaporated to give 1.6 g (25% yield) of the free phenol, 3-(N-ethylcarboxamido)-7-hydroxy-3,4-dihydrocoumarin, as a white solid, m.p. 222°–224° C.

A solution of 400 mg (1.7 mMol) of this phenol in 4 mL of pyridine containing 0.4 mL of acetic anhydride was stirred at room temperature for 25 minutes. Solvent was removed under reduced pressure to leave the acetate ester as a white solid, m.p. 135°–138° C. Without further characterization, 310 mg of it was dissolved in 6 mL of CH$_2$Cl$_2$ and added dropwise to a −30° C. solution of 310 mg (1.75 mMol) of phenylselenyl chloride in CH$_2$Cl$_2$ containing 130 mg (1.65 mMol) of pyridine. After 45 minutes, the reaction was allowed to warm to room temperature. It was applied directly to a column of 100 g of silica gel and eluted with 19:1 (v/v) CH$_2$Cl$_2$:THF. Twenty-one mL fractions were collected. Fractions 14–21 were pooled and evaporated to give 310 mg (50% yield) of 7-acetoxy-3-(N-ethylcarboxamido)-3-phenylselenyl-3,4-dihydrocoumarin (22) as a white solid, m.p. 173°–175° C.

Sensitivity of Indicator Compounds to Hydrogen Peroxide

The indicator compounds indicated in the Table below were each dissolved in ethanol (100%) to give a homogeneous solution of 1-10 mM. Serial dilutions in pH 7.0, 0.10M sodium phosphate buffer were made to allow 100 μM in 2.00 mL final reaction volume. To a solution of 40.0 μL of 1.0 mg/mL horseradish peroxidase (POD) in 0.10 M sodium phosphate buffer, pH 7.0, at 37° [with addition of 5 μL of 8 mg/mL acetylesterase (A-7900, Sigma Chemical Co., St. Louis, Mo.) for compounds 21 and 22] was added 2.00 nanomoles (nmols) of indicator compound in buffer solution. The fluorescence at 450 nm (400 nm excitation) was monitored over a 100 second span at 37° C. A portion (2.00 nmols) of cold (0° C.) hydrogen peroxide solution (23.3 μL of $8.6 \times 10^{-5}$ M $H_2O_2$ in cold water for compound 13, 100.0 μL of $2.0 \times 10^{-5}$ M $H_2O_2$ freshly diluted in cold buffer for compounds 21 and 22, and 11.7 μL of $8.6 \times 10^{-5}$ M $H_2O_2$ in cold water for compounds 4, 16, 19 and 20) was then added, and the fluorescence at 450 nm (400 nm excitation) was monitored over a ten minute span at 37°. Values were obtained in photons/second with all slits set at 2 nanometer (nm) width. A 50 nM solution of 7-hydroxy-3-(N-ethylcarboxamide)coumarin at 37° in 0.1 M sodium phosphate buffer, pH 7.50, was used as a fluorescence reference standard (U.S. Pat. No. 4,273,715).

Fluorescence was measured in quartz cuvettes on an SLM 8000 spectrofluorometer (SLM Instruments, Inc., Urbana, Ill. A Hewlett Packard 9815A computer was used to process spectra.

The results are given in the Table below.

| Relative Fluorescence of Indicator Compounds | | | | | | |
|---|---|---|---|---|---|---|
| | Time (seconds) | | | | | |
| Compound | 0 | 25 | 50 | 100 | 200 | 600 |
| 4 | 230 | 4178 | 4471 | 4471 | 4471 | 4471 |
| 13 | 1816 | 9373 | 9503 | 9763 | 9984 | 10063 |
| 16 | 326 | 600 | 750 | 1210 | 1970 | 2550 |
| 19 | 235 | 431 | 574 | 953 | 1984 | 2676 |
| 20 | 97 | 39200 | 39200 | 39200 | 40200 | 41920 |
| 21* | 235 | 1172 | 2130 | 2382 | 2421 | 2434 |
| 22* | 683 | 12041 | 17313 | 19787 | 20047 | 20177 |

*0.24 units acetylesterase added

What is claimed is:

1. A compound of the formula:

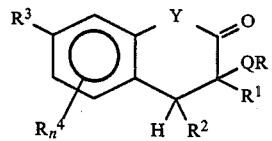

wherein Q is sulfur or selenium, R is lower alkyl phenyl, substituted phenyl or pyridyl; $R^1$ is hydrogen, cyano, carboxyl, lower alkyl, lower alkenyl, phenyl, lower carboalkoxy, lower carbophenoxy, or lower carboxamide; $R^2$ is hydrogen, lower alkyl, lower alkenyl, or phenyl; $R^3$ is —OH, or —$NR^6R^7$ where $R^6$ and $R^7$, which can be the same or different, are hydrogen or lower alkyl; n is an integer from 0 through 3; $R^4$, which can be the same or different when n=2 or 3, is halo, lower alkyl, lower alkenyl, lower alkoxy, or phenyl; and Y is >N—$R^8$ where $R^8$ is hydrogen or lower alkyl.

2. The compound of claim 1 where R is phenyl or halo-substituted or nitro-substituted phenyl.
3. The compound of claim 2 wherein Q is selenium.
4. The compound of claim 2 wherein Q is sulfur.
5. The compound of claim 2 wherein $R^3$ is OH.
6. The compound of claim 2 wherein $R^3$ is —$NR^6R^7$ wherein $R^6$ and $R^7$, which can be the same or different, are hydrogen or lower alkyl.
7. The compound of claim 6 wherein n=0.
8. The compound of claim 6 wherein Y is >N—$R^8$ where $R^8$ is hydrogen or lower alkyl.
9. The compound of claim 8 wherein n=0.
10. A compound of the formula:

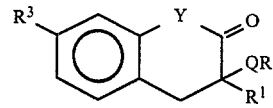

wherein Q is sulfur or selenium, R is methyl, phenyl, nitro-substituted phenyl, halo-substituted phenyl, or pyridyl; $R^1$ is hydrogen, cyano, or —$COOR^9$, —$CONHR^9$, or —$CON(R^9)_2$ where $R^9$ is hydrogen, lower alkyl, or phenyl; $R^3$ is —OH or —$NR^6R^7$ where $R^6$ and $R^7$, which can be the same or different, are hydrogen or lower alkyl; and Y is >N—$R^8$ where $R^8$ is hydrogen or lower alkyl.

11. The compound of claim 10 wherein Q is selenium.
12. The compound of claim 11 wherein R is methyl.
13. The compound of claim 11 wherein R is phenyl.
14. The compound of claim 11 wherein R is nitro-substituted phenyl.
15. The compound of claim 11 wherein R is halo-substituted phenyl.
16. The compound of claim 11 wherein $R^1$ is —$CONHR^9$ or —$COOR^9$ wherein $R^9$ is hydrogen, lower alkyl or phenyl.
17. The compound of claim 10 wherein Q is sulfur.
18. The compound of claim 17 wherein R is nitro-substituted phenyl.
19. The compound of claim 17 wherein R is halo-substituted phenyl.
20. The compound of claim 17 wherein $R^1$ is —$CONHR^9$ or —$COOR^9$ wherein $R^9$ is hydrogen, lower alkyl or phenyl.

* * * * *